United States Patent
Liu et al.

(10) Patent No.: US 9,328,084 B2
(45) Date of Patent: May 3, 2016

(54) NITROGEN-CONTAINING BIPHENYL COMPOUNDS, PHARMACEUTICAL COMPOSITIONS OF SAME, PREPARATION METHODS AND ANTI-HIV-1 USES THEREOF

(75) Inventors: Jingping Liu, Kunming (CN); Handong Sun, Kunming (CN); Hongbin Zhang, Kunming (CN); Yongtang Zheng, Kunming (CN); Weilie Xiao, Kunming (CN); Jianxin Pu, Kunming (CN); Ruirui Wang, Kunming (CN); Liumeng Yang, Kunming (CN)

(73) Assignees: Kunming Institute of Botany, The Chinese Academy of Sciences, Kunming (CN); Yunnan University, Kunming (CN); Kunming Institute of Zoology, The Chinese Academy of Sciences, Kunming (CN)

( * ) Notice: Subject to any disclaimer, the term of this patent is extended or adjusted under 35 U.S.C. 154(b) by 107 days.

(21) Appl. No.: 13/880,487

(22) PCT Filed: Oct. 13, 2011

(86) PCT No.: PCT/CN2011/080718
§ 371 (c)(1),
(2), (4) Date: Aug. 9, 2013

(87) PCT Pub. No.: WO2012/051912
PCT Pub. Date: Apr. 26, 2012

(65) Prior Publication Data
US 2013/0331390 A1    Dec. 12, 2013

(30) Foreign Application Priority Data

Oct. 20, 2010  (CN) .......................... 2010 1 0512452

(51) Int. Cl.
*C07D 317/68* (2006.01)
*A61K 31/5377* (2006.01)

(52) U.S. Cl.
CPC ................................... *C07D 317/68* (2013.01)

(58) Field of Classification Search
None
See application file for complete search history.

(56) References Cited

FOREIGN PATENT DOCUMENTS

| CN | 102010398 A | 4/2011 |
| WO | WO2007/087442 A2 | 8/2007 |

OTHER PUBLICATIONS

Glover et al., Journal of the Chemical Society, Perkin Transactions 1: Organic and Bio-Organic Chemistry (1972-1999), (1981), No. 3, pp. 842-848.*
Uehling et al., J. Med. Chem., 2006, 49 (9), pp. 2758-2771.*
Fumitoshi, K. et al., A Ruthenium-Catalyzed Reaction of Aromatic Ketones with Arylboronates: A New Method for the Arylation of Aromatic Compounds via C—H Bond Cleavage, J AM. Chem Soc., vol. 125, No. 7, pp. 1698-1699, Jan. 25, 2003.
Fumitoshi, K et al., A Ruthenium-Catalyzed Funcitonalization of Aryl Carbon—Oxygen Bonds in Aromatic Ethers with Organoboron Compounds, J. AM. Chem Soc , vol. 126, No. 9, pp. 2706-2707, Feb. 12, 2004.
Satoshi, U et al., Ruthenium-Catalyzed Carbon—Carbon Bond Formation via the Cleavage of an Unreactive Aryl Carbon—Nitrogen Bond in Aniline Derivatives with Organoboronates, J AM. Chem. Soc., vol. 129, No. 19, pp. 6098-6099, Apr. 20, 2007.
Shun, H et al., Control of Product Selectivity by a Styrene Additive in Ruthenium-Catalyzed C—H Arylation, vol. 12, No. 22, pp. 5318-5321, Oct. 27, 2010.
Siddiqui, M. A. et al., The directed metalation connection to aryl-aryl cross coupling Regiospecific synthesis of phenanthridines, phenanthridinones and the biphenyl alkaloid ismine, Tetrahedron Letters, vol. 29, No. 43, pp. 5463-5466, Dec. 31, 1988.

* cited by examiner

*Primary Examiner* — Alicia L Otton
(74) *Attorney, Agent, or Firm* — Honigman Miller Schwartz and Cohn LLP; Thomas A. Wootton, Esq.; Jonathan P. O'Brien

(57) ABSTRACT

Nitrogen-containing biphenyl compounds as represented by formula (I), pharmaceutically acceptable salts or derivatives thereof, pharmaceutical compositions, and preparation methods therefore, and anti-HIV-1 use of the compound. Each substituent group in formula (I) is as defined in the description.

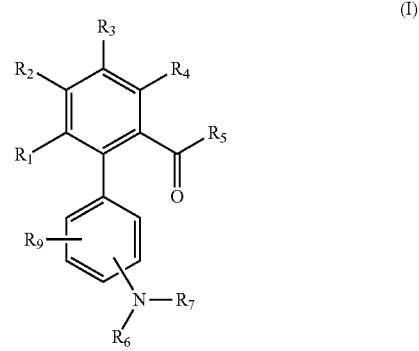

6 Claims, No Drawings

NITROGEN-CONTAINING BIPHENYL COMPOUNDS, PHARMACEUTICAL COMPOSITIONS OF SAME, PREPARATION METHODS AND ANTI-HIV-1 USES THEREOF

This U.S. patent application claims the benefit of PCT application no. PCT/CN2011/080718, filed on Oct. 13, 2011, which claims priority to Chinese Application Ser. No. 201010512452, filed Oct. 20, 2010. The entire contents of the aforementioned applications are incorporated herein by reference in their entireties.

TECHNICAL FIELD

The present invention belongs to pharmaceutical field and in particular relates to nitrogen-containing biphenyl compounds having the structural formulae (I) and (II), pharmaceutical compositions comprising the compounds as active ingredient and a pharmaceutically acceptable carrier, methods for their preparation and their use in the preparation of anti-HIV (HIV-1) drug.

BACKGROUND ART

Since the first case report in 1981, AIDS quickly spreads to countries around the world. So far, there is still no available effective anti-HIV vaccine, so the development of anti-AIDS drugs is still the most prospective route for the treatment of AIDS. At present, anti-AIDS drugs mainly include the following three categories: nucleotide antiviral drugs, transcriptase inhibitors and protease inhibitors. However, because of their high price (more than two or three hundred thousand Yuan is needed for each person each year), and relatively great side effects, these drugs are beyond the reach of the average family. Therefore, it is urgent to develop an anti-AIDS drug that is simple to use, low price, highly potent, and low toxicity. In recent years, natural products have shown promising results in the treatment of AIDS. Until now, it has been that there are more than 100 kinds of natural products which have good anti-HIV activity, such as: glycyrrhizin, hypericin, curcumin, soy saponins, camptothecin, lentinan, smallpox protein and so on.

Lignans, which are isolated from a traditional Chinese medicine—Schisandra by the applicant in recent years, show a very strong inhibitory effect on HIV integrase, and are able to inhibit the transcription of HIV-1, which can be developed to be anti-AIDS drugs (CN1634031A; CN1931151A; CN101318950A). Also, these natural products can be used as a lead compound, and serve as a template for the design of new drugs having a stronger biological activity. To date, there is no report in the prior art relating to nitrogen-containing biphenyl compounds, nor is there any report relating to use of this class of compounds as anti-AIDS drugs.

CONTENTS OF THE INVENTION

The object of the present invention is to provide a class of nitrogen-containing biphenyl compound having anti-HIV activity, to provide a pharmaceutical composition comprising said compound and a pharmaceutically acceptable carrier, and to provide methods for preparing said compound and its pharmaceutical composition. Another object of the present invention is to provide use of the nitrogen-containing biphenyl compound in the preparation of a drug for the treatment and prevention of AIDS. Still another object of the present invention is to provide a method for the treatment and prevention of AIDS, which method comprises administering to patients the nitrogen-containing biphenyl compound of the present invention.

The above objects of the present invention are realized by the following technical solutions:

The present invention provides a nitrogen-containing biphenyl compound having the following structural formula (I) or (II):

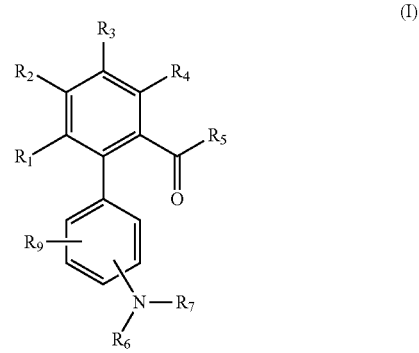

(I)

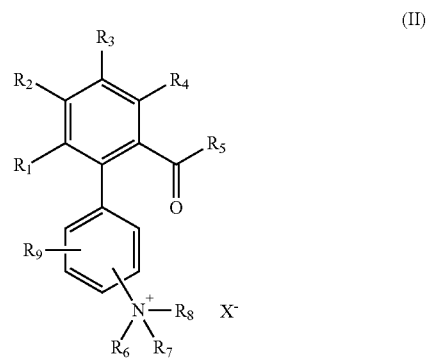

(II)

wherein $R_1$, $R_2$, $R_3$ and $R_4$ are selected from the group consisting of H, OH, OCH$_2$Ph, OR, F, Cl, Br and I, or $R_1$ and $R_2$ together form —OCH$_2$O—, or $R_2$ and $R_3$ together form —OCH$_2$O—, or $R_3$ and $R_4$ together form —OCH$_2$O—;

$R_5$ is selected from the group consisting of H, aliphatic hydrocarbyl, aromatic hydrocarbyl, OH, OCH$_2$Ph, OR and NR$_2$;

$R_6$ and $R_7$ are selected from the group consisting of H, aliphatic hydrocarbyl containing 1-15 carbon atoms, CH$_2$Ph, aromatic hydrocarbyl and RCO, or $R_6$ and $R_7$ together form —(CH$_2$)$_n$—, wherein n=2-10, or $R_6$ and $R_7$ together form —CH$_2$CH$_2$OCH$_2$CH$_2$—;

$R_8$ is selected from the group consisting of H, aliphatic hydrocarbyl, CH$_2$Ph and aromatic hydrocarbyl;

$R_9$ is selected from the group consisting of H, aliphatic hydrocarbyl and aromatic hydrocarbyl;

R is selected from the group consisting of aliphatic hydrocarbyl and aryl;

X is selected from the group consisting of F, Cl, Br, I, OH, SO$_4$ and NO$_3$.

In the nitrogen-containing biphenyl compound, the nitrogen atom linked to the radicals $R_6$, $R_7$ is located in any position of the benzene ring where it is present.

In one embodiment of the present invention, $R_1$ is selected from the group consisting of OH, $OCH_2Ph$ and OR, preferably $OCH_3$ or $OCH_2CH_3$; $R_2$ and $R_3$ together form —$OCH_2O$—; $R_5$ is selected from the group consisting of $OCH_2Ph$, $OCH_3$ and $OCH_2CH_3$; $R_6$ and $R_7$ are selected from the group consisting of aliphatic hydrocarbyl containing 1-10 carbon atoms; $R_8$ is selected from the group consisting of H, $CH_2Ph$ and aliphatic hydrocarbyl; $R_9$ is selected from the group consisting of H and aliphatic hydrocarbyl; X is Cl.

In one embodiment of the present invention, $R_1$ is $OCH_3$.

In one embodiment of the present invention, $R_2$ and $R_3$ together form —$OCH_2O$—.

In one embodiment of the present invention, $R_5$ is $OCH_3$.

In one embodiment of the present invention, $R_6$ and $R_7$ are methyl.

In one embodiment of the present invention, $R_8$ is $CH_2Ph$.

In one embodiment of the present invention, $R_9$ is methyl.

In one embodiment of the present invention, X is Cl.

DEFINITIONS

As used herein, the term "aliphatic hydrocarbyl" means a straight-chain (i.e., non-branched) or branched hydrocarbon chain that is completely saturated or that contains one or more units of unsaturation but is non-aromatic. Unless otherwise specified, the aliphatic hydrocarbyl contains 1-15 aliphatic carbon atoms ($C_{1-15}$ aliphatic hydrocarbyl). In one embodiment, the aliphatic hydrocarbyl contains 1-10 aliphatic carbon atoms ($C_{1-10}$ aliphatic hydrocarbyl). In another embodiment, the aliphatic hydrocarbyl contains 1-8 aliphatic carbon atoms ($C_{1-8}$ aliphatic hydrocarbyl). In still another embodiment, the aliphatic hydrocarbyl contains 1-6 aliphatic carbon atoms ($C_{1-6}$ aliphatic hydrocarbyl). In still another embodiment, the aliphatic hydrocarbyl contains 1-4 aliphatic carbon atoms ($C_{1-4}$ aliphatic hydrocarbon). The aliphatic hydrocarbyl may be straight chain or branched chain alkyl, alkenyl or alkynyl group. Specific examples of aliphatic hydrocarbyl include, but are not limited to, methyl, ethyl, n-propyl, iso-propyl, n-butyl, tert-butyl, vinyl, n-butenyl, ethynyl and the like.

As used herein, the term "alkyl" means a saturated straight-chain or branched-chain hydrocarbyl. As used herein, the term "alkenyl" refers to a straight-chain or branched-chain hydrocarbyl containing one or more double bonds. As used herein, the term "alkynyl" means a straight-chain or branched-chain hydrocarbyl containing one or more triple bonds.

As used herein, the term "aromatic hydrocarbyl" means an unsaturated aromatic carbocyclic group having one single ring or two or more fused rings having 6-18 carbon atoms ($C_{6-18}$ aromatic hydrocarbyl). The aromatic hydrocarbyl preferably has 6-10 carbon atoms ($C_{6-10}$ aromatic hydrocarbyl), more preferably having 6 carbon atoms ($C_6$ aromatic hydrocarbyl). Typical examples of the "aromatic hydrocarbyl" include, but are not limited to, phenyl, naphthyl, anthryl and the like.

The preferred nitrogen-containing biphenyl compounds of the present invention are compounds 5-12 having the following structural formulae:

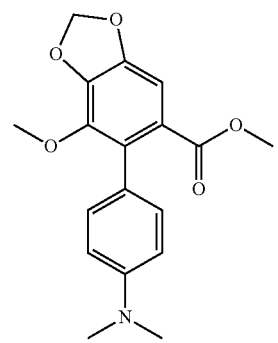

Compound 5

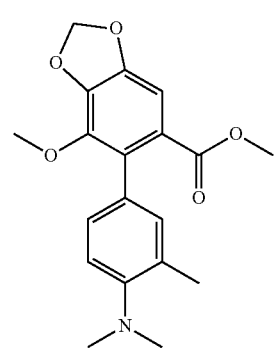

Compound 6

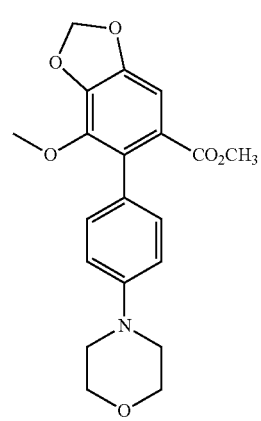

Compound 7

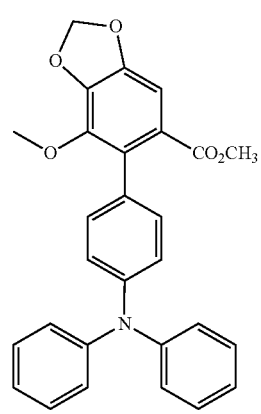

Compound 8

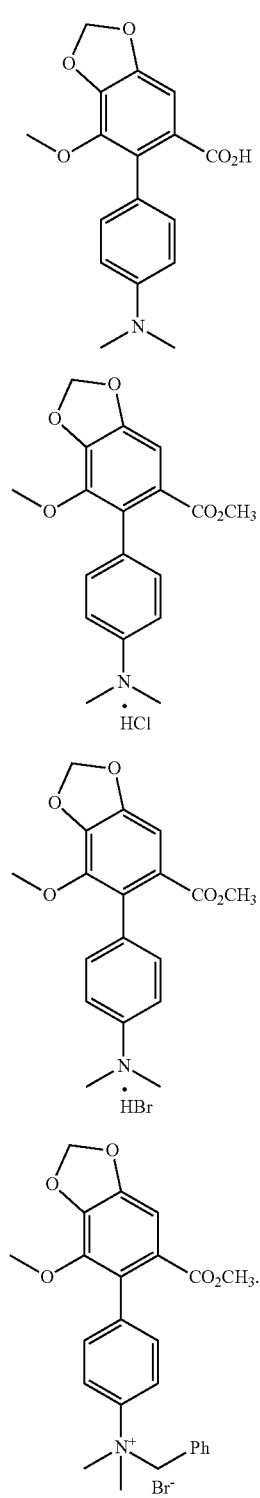

Compound 9

Compound 10

Compound 11

Compound 12

The present invention also provides a method for the preparation of the nitrogen-containing biphenyl compound of the structural formula (I), which comprises:

coupling Compound 1 and Compound 2 by metallic catalysis to obtain the nitrogen-containing biphenyl compound of the structural formula (I), wherein the reaction formula is shown as follows:

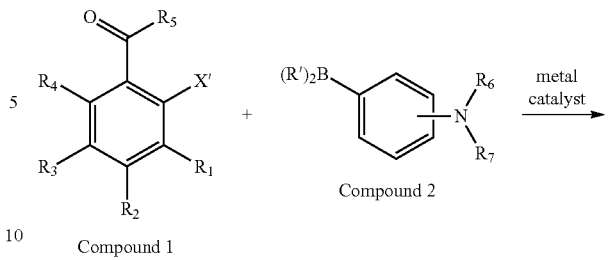

wherein:

X' is F, Cl, Br or I;

R' is an aliphatic or aromatic hydrocarbyl, or two R's together form —OC(CH$_3$)$_2$—C(CH$_3$)$_2$O—;

the metal catalyst is palladium, platinum, rhodium, ruthenium, lithium, copper, magnesium, nickel or zinc; and $R_1$-$R_7$ are as defined above in the formula (I) and formula (II); and optionally, the obtained nitrogen-containing biphenyl compound of the structural formula (I) is subjected to a corresponding salt-forming reaction, to obtain the nitrogen-containing biphenyl compound of the structural formula (II).

A general illustrative preparation method of the nitrogen-containing biphenyl compound of the structural formula (I) is described as follows: mixing Compound 1 (0.1 mmol) and Compound 2 (0.2-0.5 mmol), then adding Pd(OAc)$_2$ (0.01-0.05 mmol), Bu$_4$NBr (0.15 mmol), K$_2$CO$_3$ (0.3 mmol) and 3 mL THF-H$_2$O (V$_{THF}$/V$_{H2O}$=1) to the resultant mixture, heating the mixture to about 70° C., reacting for about 4 hours, cooling the mixture to room temperature, filtering and concentrating the reaction solution, and purifying by a silica gel column, to obtain the compound of the structural formula (I).

A general illustrative preparation method of the nitrogen-containing biphenyl compound of the structural formula (II) is described as follows: the compound of the structural formula (I) obtained by the above method is subjected to a corresponding salt-forming reaction, to obtain a variety of ammonium salts or quaternary ammonium salts, i.e., the compounds of the structural formula (II).

The present invention also provides a pharmaceutical composition which comprises the compound of the structural formula (I), the compound of the structural formula (II), in particular one of the compounds 5-12, of the present invention as an active ingredient, and at least one pharmaceutically acceptable carrier.

The present invention also provides use of the nitrogen-containing biphenyl compound of the present invention in the preparation of a drug for the treatment or prevention of AIDS.

As used herein, the pharmaceutically acceptable carrier refers to a conventional pharmaceutical carrier in the pharmaceutical field, such as: diluents, excipients such as water, fillers such as starch, sucrose and the like; binders such as cellulose derivatives, alginates, gelatin, and polyvinyl pyrrolidone; wetting agents such as glycerol; disintegrating agents such as agar, calcium carbonate and sodium bicarbonate; absorption accelerators such as quaternary ammonium compounds; surface active agents such as cetyl alcohol; adsorption carriers such as kaolin and bentonite; lubricants such as talc, calcium and magnesium stearate, and polyethylene glycol and the like. Furthermore, other auxiliary agents, such as flavoring agents, sweeteners and the like, can also be added to the composition.

The compound of the present invention can be applied to patients in need of such treatment in the form of composition by oral, nasal inhalation, rectal or parenteral administration. For oral administration, it can be made into conventional solid preparations such as tablets, powders, granules, capsules and the like, or made into liquid preparations, such as water or oil suspensions or other liquid preparations such as syrups, elixirs and the like; for parenteral administration, it can be made into injection solutions, aqueous or oily suspensions and the like. Preferably, the composition is in the form of tablets, capsules and injections.

The various dosage forms of the pharmaceutical composition of the present invention can be prepared in accordance with conventional production method in pharmaceutical field. For example, the active ingredient is mixed with one or more carriers, and then formed into the desired dosage form.

The pharmaceutical composition of the present invention comprises the active ingredient in a weight percent of preferably 0.1%-99.5%, and most preferably 0.5%-95%.

The dosage of the compound of the present invention can vary according to the route of administration, the patient's age, body weight, the type and severity of the disease to be treated and the like, and the daily dosage thereof may be 0.01-10 mg/kg body weight, preferably 0.1-5 mg/kg body weight. It can be administered once or several times.

MODE OF CARRYING OUT THE INVENTION

The following examples are exemplifying, but not limiting, the method of the present invention. Other modifications and adaptive changes on various conditions and parameters, which are obvious to a person skilled in the art, are all included within the spirit and scope of the present invention.

EXAMPLE 1

Preparation method of nitrogen-containing biphenyl compound of the present invention can be generally summarized as follows:

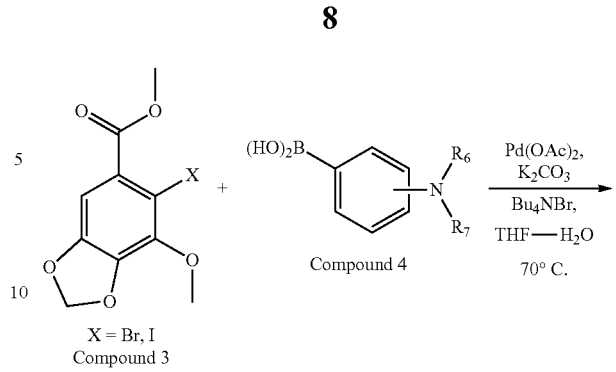

X = Br, I
Compound 3

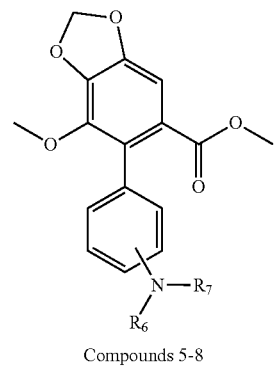

Compounds 5-8

Compound 3 (0.1 mmol) and Compound 4 (0.2-0.5 mmol) were put in a 25 mL round-bottomed flask, followed by addition of Pd(OAc)$_2$ (0.01-0.05 mmol), Bu$_4$NBr (0.15 mmol), K$_2$CO$_3$ (0.3 mmol) and 3 mL THF-H$_2$O (V$_{THF}$/V$_{H2O}$=1). The mixture was heated to 70° C. and the reaction was carried out for 4 hours. The reaction solution was cooled to room temperature, filtered, concentrated, and purified by silica gel column to give compounds 5-8 in Example 2-5.

Compound 4 is purchased from Acros or Sigma-Aldrich Company.

Compound 3 is obtained by the following synthetic route:

(a) Synthesis of Bromo Compound 3:

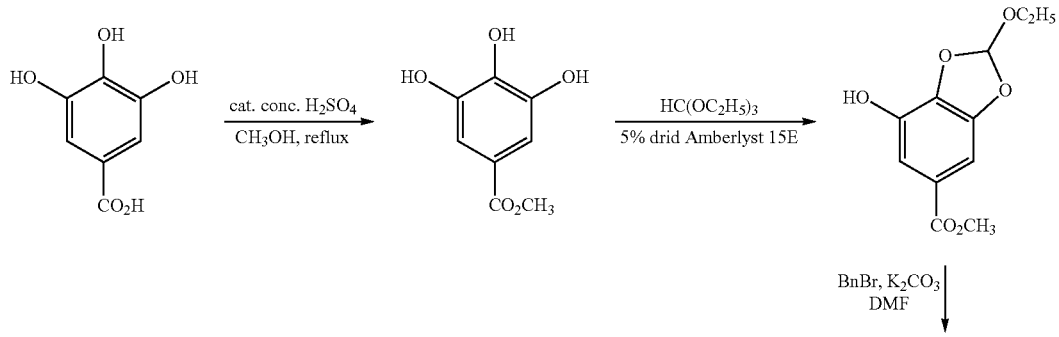

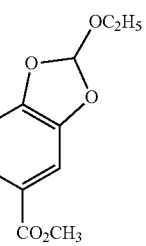 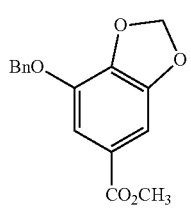 
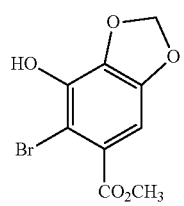 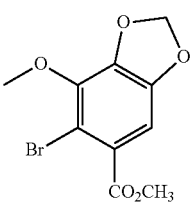
Bromo compound 3
Bromo Compound 3 was synthesized using gallic acid as a starting material, through esterification of carboxyl group, etherification of phenolic hydroxyl group, bromination of benzene ring, removal of benzyl protecting group, and final methyl etherification.
(b) Synthesis of Iodo Compound 3:
 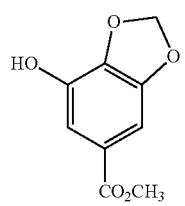 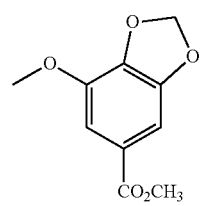
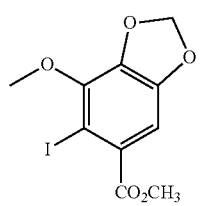  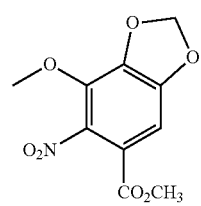
Iodo compound 3

Iodo Compound 3 was synthesized using one intermediate compound obtained during the synthesis of bromo Compound 3 as a starting material, through removal of benzyl protecting group, methyl etherification, nitration of benzene ring, reduction of nitro group into amino group, and final Sandmeyer reaction (amino group was firstly converted to a diazonium salt in the presence of concentrated HCl+NaNO$_2$, and then, after the addition of an aqueous solution of KI, the iodo compound was obtained).

EXAMPLE 2

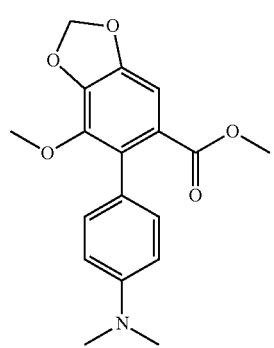

Compound 5

Bromo Compound 3 (0.1 mmol) obtained in Example 1 and 4-(N,N-dimethylamino)phenylboronic acid (CAS: 28611-39-4) (0.2 mmol) were put in a 25 mL round-bottomed flask, followed by addition of Pd(OAc)$_2$ (0.01 mmol), Bu$_4$NBr (0.15 mmol), K$_2$CO$_3$ (0.3 mmol), and 3 mL THF-H$_2$O (V$_{THF}$/V$_{H2O}$=1). The mixture was heated to 70° C. and the reaction was carried out for 4 hours. The reaction solution was cooled to room temperature, filtered, concentrated, and purified by silica gel column to give Compound 5.

The relevant test data were as follows: $^1$H-NMR (300 MHz, CDCl$_3$): δ=7.09 (d, 2H), 7.03 (s, 1H), 6.74 (d, 2H), 6.02 (s, 2H), 3.77 (s, 3H), 3.57 (s, 3H), 2.98 (s, 6H); $^{13}$C-NMR (75 MHz, CDCl$_3$): δ=168.40, 149.49, 147.67, 141.44, 140.13, 131.16, 130.20, 125.83, 124.16, 111.74, 104.38, 101.74, 60.00, 51.90, 40.48.

EXAMPLE 3

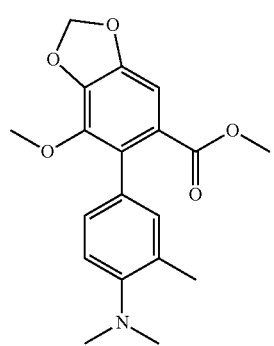

Compound 6

Bromo Compound 3 (0.1 mmol) obtained in Example 1 and 4-(N,N-dimethylamino)-3-phenylboronic acid (CAS: 919496-59-6) (0.3 mmol) were put in a 25 mL round-bottomed flask, followed by addition of Pd(OAc)$_2$ (0.02 mmol), Bu$_4$NBr (0.15 mmol), K$_2$CO$_3$ (0.3 mmol), and 3 mL THF-H$_2$O (V$_{THF}$/V$_{H2O}$=1). The mixture was heated to 70° C. and the reaction was carried out for 4 hours. The reaction solution was cooled to room temperature, filtered, concentrated, and purified by silica gel column to give Compound 6.

The relevant test data were as follows: $^1$H-NMR (300 MHz, CDCl$_3$): δ=6.92-6.95 (m, 4H), 5.97 (s, 2H), 3.70 (s, 3H), 3.45 (s, 3H), 2.66 (s, 6H), 2.26 (s, 3H); $^{13}$C-NMR (75 MHz, CDCl$_3$): δ=167.92, 149.43, 147.72, 145.77, 140.34, 131.68, 127.31, 125.93, 124.65, 123.20, 115.11, 112.24, 108.13, 101.54, 56.40, 51.86, 40.55, 16.23.

EXAMPLE 4

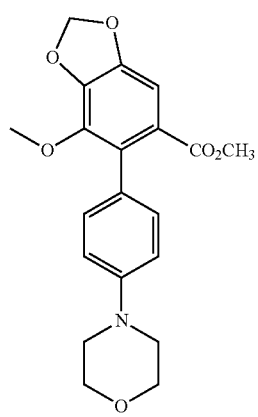

Compound 7

Iodo Compound 3 (0.1 mmol) obtained in Example 1 and 4-morpholinyl phenylboronic acid pinacol ester (CAS: 568577-88-8) (0.5 mmol) were put in a 25 mL round-bottomed flask, followed by addition of Pd(OAc)$_2$ (0.05 mmol), Bu$_4$NBr (0.15 mmol), K$_2$CO$_3$ (0.3 mmol), and 3 mL THF-H$_2$O (V$_{THF}$/V$_{H2O}$=1). The mixture was heated to 70° C. and the reaction was carried out for 4 hours. The reaction solution was cooled to room temperature, filtered, concentrated, and purified by silica gel column to give Compound 7.

The relevant test data were as follows: $^1$H-NMR (300 MHz, CDCl$_3$): δ=6.92 (s, 1H), 6.03 (s, 2H), 3.85-3.89 (t, 4H), 3.76 (s, 3H), 3.56 (s, 3H), 3.19-3.22 (t, 4H); $^{13}$C-NMR (75 MHz, CDCl$_3$): δ=168.39, 150.00, 147.92, 141.67, 140.78, 128.01, 104.52, 101.83, 66.98, 60.05, 51.95, 49.06.

EXAMPLE 5

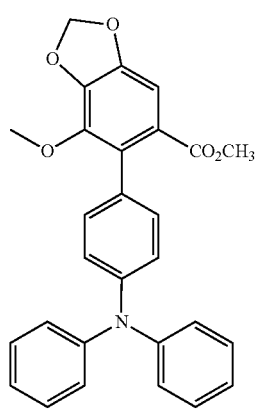

Compound 8

Iodo Compound 3 (0.1 mmol) obtained in Example 1 and 4-(N,N-diphenylamino)phenylboronic acid (CAS: 201802-67-7) (0.5 mmol) were put in a 25 mL round-bottomed flask, followed by addition of Pd(OAc)$_2$ (0.05 mmol), Bu$_4$NBr (0.15 mmol), K$_2$CO$_3$ (0.3 mmol), and 3 mL THF-H$_2$O ($V_{THF}/V_{H2O}$=1). The mixture was heated to 70° C. and the reaction was carried out for 4 hours. The reaction solution was cooled to room temperature, filtered, concentrated, and purified by silica gel column to give Compound 8.

The relevant test data were as follows: $^1$H-NMR (300 MHz, CDCl$_3$): δ=6.47-7.32 (m, 15H), 5.98 (s, 2H), 3.76 (s, 3H), 3.62 (s, 3H). $^{13}$C-NMR (75 MHz, CDCl$_3$): δ=168.55, 149.50, 148.71, 141.43, 140.32, 139.93, 131.43, 130.53, 129.11, 125.76, 124.64, 123.32, 121.11, 113.00, 107.71, 101.73, 61.11, 51.87.

EXAMPLE 6

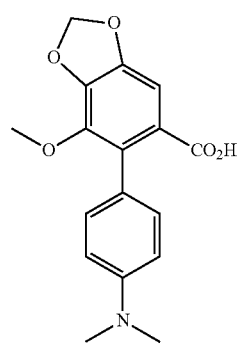

Compound 9

Compound 5 (0.01 mmol) obtained in Example 2 was put in a 10 mL round-bottomed flask, followed by addition of 2 mL methanol and 0.1 mL 40% aqueous solution of NaOH. The reaction was carried out at room temperature with stirring for 10 hours. After the starting material disappeared as detected by TLC, 10 mL saturated aqueous solution of NH$_4$Cl was added, followed by extraction with ethyl acetate twice (in an amount of about 3 mL each time). The organic phases were combined, dried with anhydrous sodium sulfate, filtered, concentrated, and recrystallized with ethyl acetate to give Compound 9.

The relevant test data were as follows: $^1$H-NMR (300 MHz, CDCl$_3$): δ=7.20 (s, 1H), 7.11 (d, 2H), 6.75 (d, 2H), 6.06 (s, 2H), 3.76 (s, 3H), 2.98 (s, 6H); $^{13}$C-NMR (75 MHz, CDCl$_3$): δ=170.34, 149.67, 147.66, 142.87, 141.34, 131.21, 130.54, 125.76, 124.21, 112.15, 105.44, 101.90, 60.01, 40.47.

EXAMPLE 7

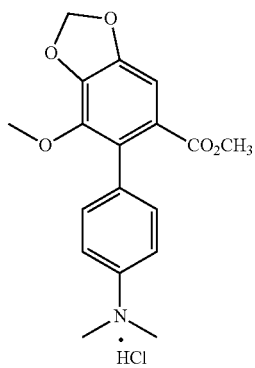

Compound 10

Compound 5 (0.01 mmol) obtained in Example 2 was put in a 10 mL round-bottomed flask, followed by addition of 5 mL ethyl ether, and addition of 0.02 mL 36% aqueous solution of HCl dropwise. The reaction was carried out at room temperature with stirring for 1 hours. The reaction solution was filtered. The resulting filter cake was washed with water for 3 times in an amount of 1 mL each time, and then rapidly washed with ethyl ether for 3 times in an amount of 1 mL each time. After drying, Compound 10 was obtained.

The relevant test data were as follows: $^1$H-NMR (300 MHz, MeOD): δ=7.66 (d, 2H), 7.37 (d, 2H), 7.13 (s, 1H), 6.12 (s, 2H), 3.81 (s, 3H), 3.57 (s, 3H), 3.36 (s, 6H); $^{13}$C-NMR (75 MHz, MeOD): δ=168.49, 150.54, 142.97, 142.36, 141.70, 140.60, 132.98, 130.34, 126.04, 120.58, 105.59, 103.83, 60.43, 52.42, 47.16.

EXAMPLE 8

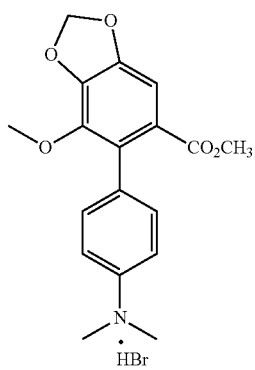

Compound 11

Compound 5 (0.01 mmol) obtained in Example 2 was put in a 10 mL round-bottomed flask, followed by addition of 5 mL ethyl ether, and addition of 0.02 mL 40% aqueous solution of HBr dropwise. The reaction was carried out at room temperature with stirring for 1 hours. The reaction solution was filtered. The resulting filter cake was washed with water for 3 times in an amount of 1 mL each time, and then rapidly washed with ethyl ether for 3 times in an amount of 1 mL each time. After drying, Compound 11 was obtained.

The relevant test data were as follows: $^1$H-NMR (300 MHz, CD$_3$COCD$_3$): δ=8.01 (d, 2H), 7.37 (d, 2H), 7.09 (s, 1H), 6.18 (s, 2H), 3.81 (s, 3H), 3.49 (s, 3H), 3.24 (s, 6H); $^{13}$C-NMR (75 MHz, CD$_3$COCD$_3$): δ=167.41, 149.91, 143.14, 141.94, 141.17, 139.82, 132.20, 129.87, 126.29, 121.17, 105.13, 103.39, 60.29, 52.07, 46.59.

EXAMPLE 9

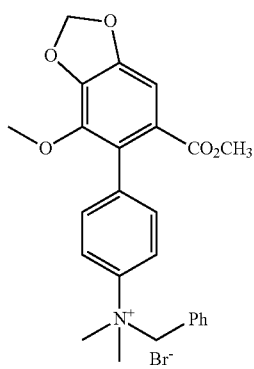

Compound 12

Compound 5 (0.01 mmol) obtained in Example 2 was put in a 10 mL round-bottomed flask, followed by addition of benzyl bromide (0.015 mmol) and 2 mL toluene. The mixture was heated to 80° C. and the reaction was carried out for 12 hours. The reaction solution was filtered. The resulting filter cake was washed with ethyl ether for 3 times in an amount of 1 mL each time. After drying, Compound 12 was obtained.

The relevant test data were as follows: $^1$H-NMR (300 MHz, MeOD): δ=7.73 (d, 2H), 7.39-7.31 (m, 5H), 7.13 (s, 1H), 7.11 (d, 2H), 6.13 (s, 2H), 5.08 (s, 2H), 3.82 (s, 3H), 3.72 (s, 6H), 3.65 (s, 3H); $^{13}$C-NMR (75 MHz, MeOD): δ=168.50, 150.55, 143.12, 142.49, 141.82, 141.41, 133.89, 132.69, 131.88, 130.22, 129.98, 129.01, 125.86, 121.88, 105.72, 103.90, 75.03, 60.51, 53.91, 52.48.

EXAMPLE 10

HIV-1 Infectious Titration Test of the Compounds 5-12 Obtained in the Above Examples Titration was conducted according to the improved method of Johnson & Byington: a stock solution of HIV-1$_{IIIB}$ was diluted by four folds in a 96-well plate, in 10 gradients with 6 repeated wells for each gradient, while setting 6 control wells. To each pore C8166 cells 50 μL (4×10$^5$/mL) was added, the final volume being 200 μL per pore. Culture was conducted at 37° C. and 5% CO$_2$. On the third day, 100 μL fresh RPMI-1640 complete culture medium was replenished. On the seventh day, HIV-1 induced Cytopathic Effect (CPE) in every well was observed using an inverted microscope, determined by whether or not Syncytium was formed in every pore. 50% Tissue Culture Infection Dose (TCID$_{50}$) of virus was calculated according to Reed & Muench method.

EXAMPLE 11

Cytotoxicity Test of the Compounds 5-12 Obtained in the Above Examples on C8166 Host Cell 100 μL of 4×10$^5$/mL C8166 cell suspension was mixed with different candidate compound solutions. Set three repeated wells. Meanwhile, set compound-free control wells. Culture was conducted at 37° C. and 5% CO$_2$ for three days. Cell toxicity was tested using MTT colorimetry. OD value was tested using EL$_x$800 ELISA instrument, with the measurement wavelength of 595 nm and the reference wavelength of 630 nm. CC$_{50}$ value (50% Cytotoxic Concentration), i.e. the concentration of compound that exhibits toxicity to 50% normal T lymphocyte cell line C8166, was calculated.

EXAMPLE 12

Inhibition Test of the Compounds 5-12 Obtained in the Above Examples on HIV-1$_{IIIB}$ Induced Cytopathic Effect (CPE) of C8166

8×10$^5$/mL C8166 cell suspension was inoculated in 50 μL/well into a 96-well cell culture plate containing compound diluted in multiple proportions in 100 μL/well, to which was then added 50 μL of HIV-1$_{IIIB}$ diluted supernatant (M.O.I. 0.0016). Set three repeated wells, at the same time, set normal cell control wells that are free of the compound. Culture was conducted at 37° C. and 5% CO$_2$ for three days. Syncytium formation was counted using an inverted microscope (100×). EC$_{50}$ (50% Effective Concentration), i.e., the concentration of the compound that inhibits 50% syncytium formation, was calculated.

EXAMPLE 13

Protective Effect of the Compounds 5-12 Obtained in the Above Examples on HIV-Infected Cells 8×10$^5$/mL MT$_4$ cell suspension was inoculated in 50 μL/well into a 96-well cell culture plate containing compound diluted in multiple proportions in 100 μL/well, to half of the wells was added 50 μL of HIV-1$_{IIIB}$ diluted supernatant (M.O.I. 0.0016), and to the other half of the wells was added 50 μL of the medium. Set two repeated wells per concentration gradient, and at the same time, set compound-free control wells and blank control wells. Culture was conducted at 37° C. and 5% CO$_2$. On the third day, 100 μL of fresh culture medium was replenished per well. On the fifth or sixth day, the survival rate of cells was tested using MTT colorimetry. OD value was tested using EL$_x$800 ELISA instrument, with the measurement wavelength of 595 nm and the reference wavelength of 630 nm. The toxicity of the compounds on normal cells and the protective effect of the compounds on HIV-1$_{IIIB}$ infected cells were calculated using formula.

EXAMPLE 14

Calculation method and formula: dose-response curve was plotted according to the experimental results; according to Reed & Muench method, 50% effective concentration (EC$_{50}$) to inhibit viruses, 50% Cytotoxic Concentration (CC$_{50}$) and anti-HIV-1 activity in the Therapeutic Index (TI) were calculated according to the formula: TI=CC$_{50}$/EC$_{50}$.

EXAMPLE 15

Anti-HIV-1 activity test results of the compounds 5-12 obtained in the above Examples (as shown in Table 1):

TABLE 1

Anti-HIV-1 activity test results of the nitrogen-containing biphenyl compounds of the present invention

| Name of the sample | toxicity ($CC_{50}$) (μg/ml) 1 | 2 | Syncytia inhibition ($EC_{50}$) (μg/ml) 1 | 2 | Therapeutic index (TI) |
|---|---|---|---|---|---|
| Compound 5 | >1250 | 411.41 | 0.44 | 0.14 | >2840.91 |
| Compound 6 | >1250 | 358.2 | 0.49 | 0.14 | >2551.02 |
| Compound 7 | 880.86 | 316.56 | 0.64 | 0.23 | 1376.35 |
| Compound 8 | 802.14 | 245.21 | 0.93 | 0.28 | 862.52 |
| Compound 9 | 649.14 | 204.55 | >25 | 7.88 | <25.97 |
| Compound 10 | >1250 | 456.38 | 0.42 | 0.15 | >2976.19 |
| Compound 11 | 71.94 | 29.43 | 0.63 | 0.26 | 114.19 |
| Compound 12 | 53.27 | 26.59 | 7.50 | 3.74 | 7.10 |

As can be seen from Table 1, Compound 5 had a very significant anti-HIV-1 activity. Meanwhile, as the substituent group on nitrogen atom of the compound increased, its activity somewhat declined. When the ester group of the compound was hydrolyzed into carboxy group (Compound 9), its activity declined notably. This indicated that the ester group imposed a notable impact on the anti-HIV-1 activity of the compound. When Compound 5 was prepared into a hydrochloride salt (Compound 10), the activity was increased, whereas the activity of its ammonium salt or quaternary ammonium salt was declined notably.

EXAMPLE 16

Tablets: one of compounds 5-12 obtained in the above Examples as an active ingredient 10 mg, lactose 180 mg, starch 55 mg, magnesium stearate 5 mg.

Preparation: the active ingredient, lactose and starch were mixed, and wetted uniformly with water; the wetted mixture was sieved and dried, and then sieved; magnesium stearate was added, and then the resulting mixture was tabletted. The tablets each weighed 250 mg, and contained the active ingredient in an amount of 10 mg.

EXAMPLE 17

Ampoules: one of compounds 5-12 obtained in the above Examples as an active ingredient 2 mg, sodium chloride 10 mg.

Preparation: the active ingredient and sodium chloride were dissolved in an appropriate amount of water for injection, then the resulting solution was filtered, and filled into ampoules under sterile conditions.

EXAMPLE 18

Capsules: one of compounds 5-12 obtained in the above Examples as an active ingredient 10 mg, lactose 187 mg, magnesium stearate 3 mg.

Preparation: the active ingredient was mixed with adjuvants, sieved, and mixed uniformly; the resulting mixture was filled into hard gelatin capsules. The capsules each weighted 200 mg, and contained the active ingredient in an amount of 10 mg.

The invention claimed is:

1. The nitrogen-containing biphenyl compound having the following structural formula (I) or (II):

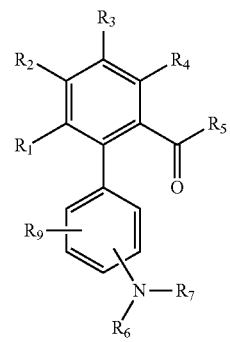
(I)

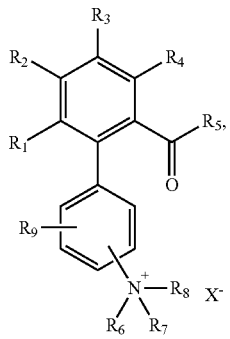
(II)

wherein $R_1$ is selected from the group consisting of OH, $OCH_2Ph$ and OR;

$R_2$ and $R_3$ together form —$OCH_2O$—;

$R_4$ is selected from the group consisting of H, OH, $OCH_2Ph$, OR, and I;

$R_5$ is selected from the group consisting of $OCH_2Ph$ and OR;

$R_6$ and $R_7$ are selected from the group consisting of aliphatic hydrocarbyl containing 1-10 carbon atoms;

$R_8$ is selected from the group consisting of H, $CH_2Ph$ and aliphatic hydrocarbyl;

$R_9$ is selected from the group consisting of H and aliphatic hydrocarbyl; R is selected from the group consisting of aliphatic hydrocarbyl and aryl;

X is Cl.

2. The nitrogen-containing biphenyl compound, hich is selected from compounds 5-12 having the following structural formulae:

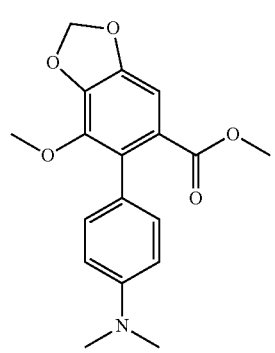
Compound 5

Compound 6
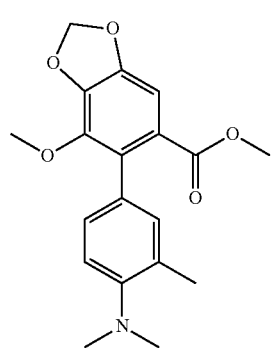
Compound 7
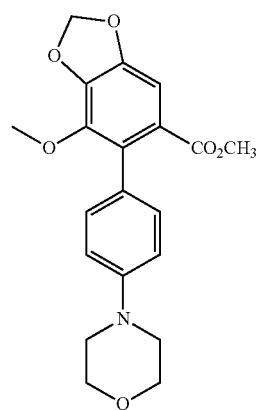
Compound 8
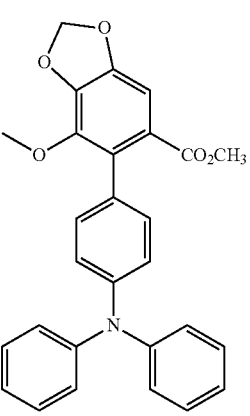
Compound 9
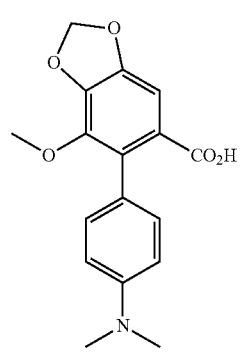
Compound 10
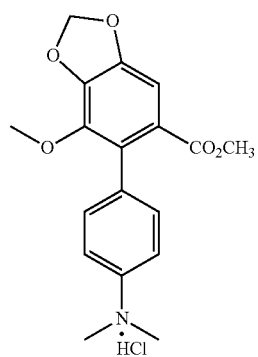
Compound 11
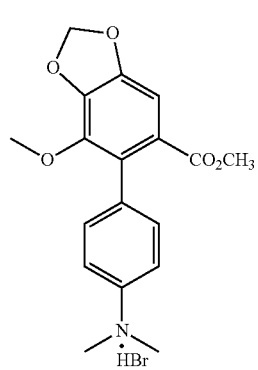
Compound 12
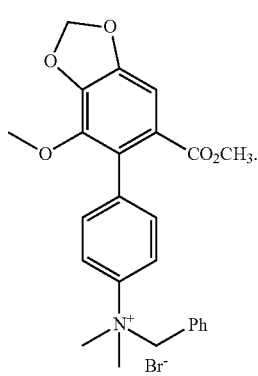
3. A pharmaceutical composition, comprising the nitrogen-containing biphenyl compound according to claim 1 and at least one pharmaceutically acceptable carrier.

4. A method for preparing the nitrogen-containing biphenyl compound
having the following structural formula (I) or (II):

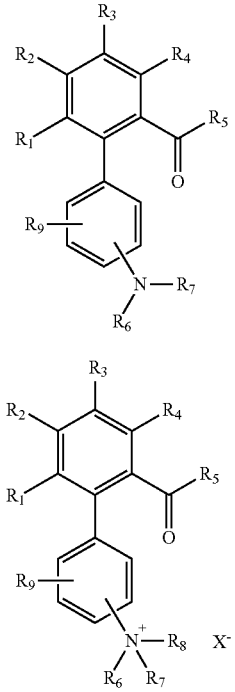

wherein
$R_1$ is selected from the group consisting of OH, OCH$_2$Ph and OR;
$R_2$ and $R_3$ together form —OCH$_2$O—;
$R_4$ is selected from the group consisting of H, OH, OCH$_2$Ph, OR, and I;
$R_5$ is selected from the group consisting of OCH2Ph and OR;
$R_6$ and $R_7$ are selected from the group consisting of aliphatic hydrocarbyl containing 1-10 carbon atoms;
$R_8$ is selected from the group consisting of H, CH$_2$Ph and aliphatic hydrocarbyl;
$R_9$ is selected from the group consisting of H and aliphatic hydrocarbyl; R is selected from the group consisting of aliphatic hydrocarbyl and aryl;
X is Cl,
which preparation comprises:
coupling Compound 1 and Compound 2 by metallic catalysis to obtain the nitrogen-containing biphenyl compound of the structural formula (I) according to the following reaction formula:

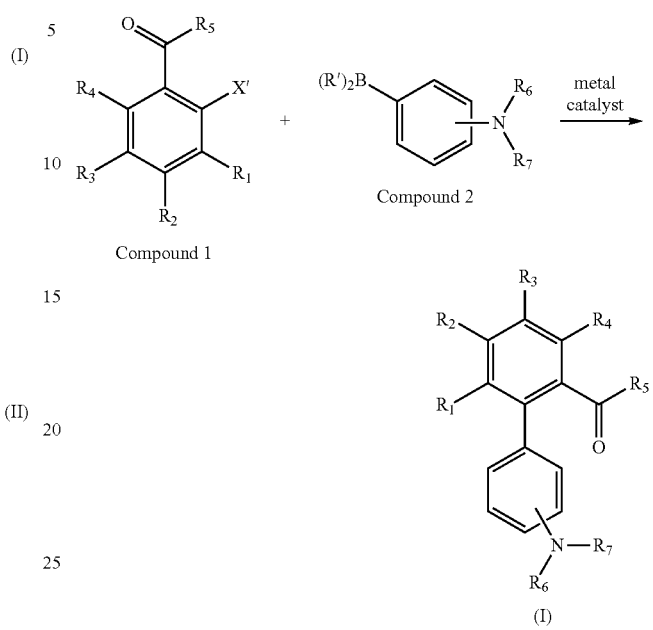

wherein:
X' is F, Cl, Br or I;
R' is an aliphatic or aromatic hydrocarbyl, or two R's together form —OC(CH$_3$)$_2$—C(CH$_3$)$_2$O—;
the metal catalyst is palladium, platinum, rhodium, ruthenium, lithium, copper, magnesium, nickel or zinc; and
optionally, the obtained nitrogen-containing biphenyl compound of the structural formula (I) is subjected to a corresponding salt-forming reaction, to obtain the nitrogen-containing biphenyl compound of the structural formula (II).

5. The method for preparing the nitrogen-containing biphenyl compound according to claim 4, comprising mixing Compound 1 and Compound 2, adding Pd(OAc)$_2$, Bu$_4$NBr, K$_2$CO$_3$ and THF-H$_2$O (V$_{THF}$/V$_{H2O}$=1) to the resultant mixture, heating the mixture to 70° C., reacting for 4 hours, cooling the mixture to room temperature, filtering and concentrating the reaction solution, and purifying by a silica gel column, to obtain the compound of the structural formula (I).

6. A method for the treatment of AIDS, which comprises the step of administering to a patient the nitrogen-containing biphenyl compound according to claim 1.

* * * * *